US00PP29296P3

(12) United States Plant Patent
Garcia-Mercado

(10) Patent No.: US PP29,296 P3
(45) Date of Patent: May 15, 2018

(54) *LIATRIS* PLANT NAMED 'BCLT-08.001'

(50) Latin Name: ***Liatris spicata* (L.) Willd.**
Varietal Denomination: BCLT-08.001

(71) Applicant: Rogelio Garcia-Mercado, Half Moon Bay, CA (US)

(72) Inventor: Rogelio Garcia-Mercado, Half Moon Bay, CA (US)

( * ) Notice: Subject to any disclaimer, the term of this patent is extended or adjusted under 35 U.S.C. 154(b) by 13 days.

(21) Appl. No.: 14/999,280

(22) Filed: Apr. 18, 2016

(65) Prior Publication Data

US 2017/0303454 P1 Oct. 19, 2017

(51) Int. Cl.
*A01H 5/02* (2018.01)

(52) U.S. Cl.
USPC ..... Plt./263.1
CPC ..... *A01H 5/02* (2013.01)

(58) Field of Classification Search
USPC ..... Plt./263.1
See application file for complete search history.

*Primary Examiner* — Susan McCormick Ewoldt
(74) *Attorney, Agent, or Firm* — James R. Cypher; Charles R. Cypher

(57) ABSTRACT

A new and distinct cultivar of *Liatris spicata* (L.) Willd. named 'BCLT-08.001' originated as an open controlled cross of *Liatris spicata* (L.) Willd. 'Cobalt'. The present variety is similar to its parents in that it is a relatively compact plant with strong stems. It differs from its parents in that its lower leaves are resistant to blackening and are so wavy that they can be corkscrew in form. It has bright inflorescences that are resistant to drooping, and good commercial characteristics.

3 Drawing Sheets

Botanical classification: *Liatris spicata* (L.) Willd.
Variety denomination: 'BCLT-08.001'.

BACKGROUND OF THE INVENTION

This invention relates to a new and distinct cultivar of the Compositae family. The botanical name of the plant is *Liatris spicata* (L.) Willd. 'BCLT-08.001'.

The new cultivar originated as a seedling from the controlled crosses of the commercial variety *Liatris spicata* var. 'Cobalt'. The parent was a dwarf variety that was openly pollinated. The present variety is similar to its parent in that it is a relatively compact plant with strong stems. It differs from its parent in that its lower leaves are resistant to black spotting from fungal diseases and are so wavy that they can be corkscrew in form. It also differs in that it has bright inflorescences that are resistant to drooping.

The variety 'BCLT-08.001' has attractive, bright inflorescences, compact growth habit, and good commercial characteristics.

The new cultivar 'BCLT-08.001' has been successfully asexually reproduced under controlled environmental conditions at a nursery in Half Moon Bay, Calif. under the direction of the inventor with its distinguishing characteristics remaining stable.

Asexual reproduction was first accomplished when vegetative cuttings were taken from the initially selected plant. Examination of asexually reproduced, successive generations grown in Half Moon Bay, Calif. show that the combination of characteristics as herein disclosed for 'BCLT-08.001' remains firmly fixed.

DESCRIPTION OF THE DRAWINGS

The accompanying drawings consist of color photographs that show the typical plant form, including the inflorescence and foliage.

DESCRIPTION OF THE NEW PLANT

Figure 1:
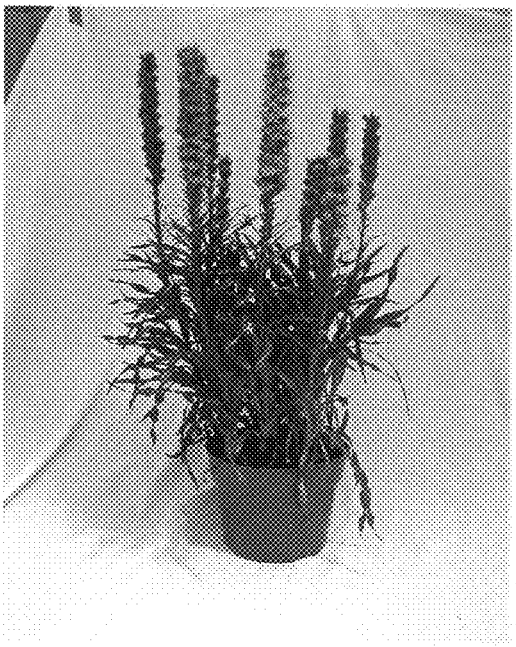
FIG. 1 is a view of the entire plant showing its form, growth habit and foliage.
Figure 2:
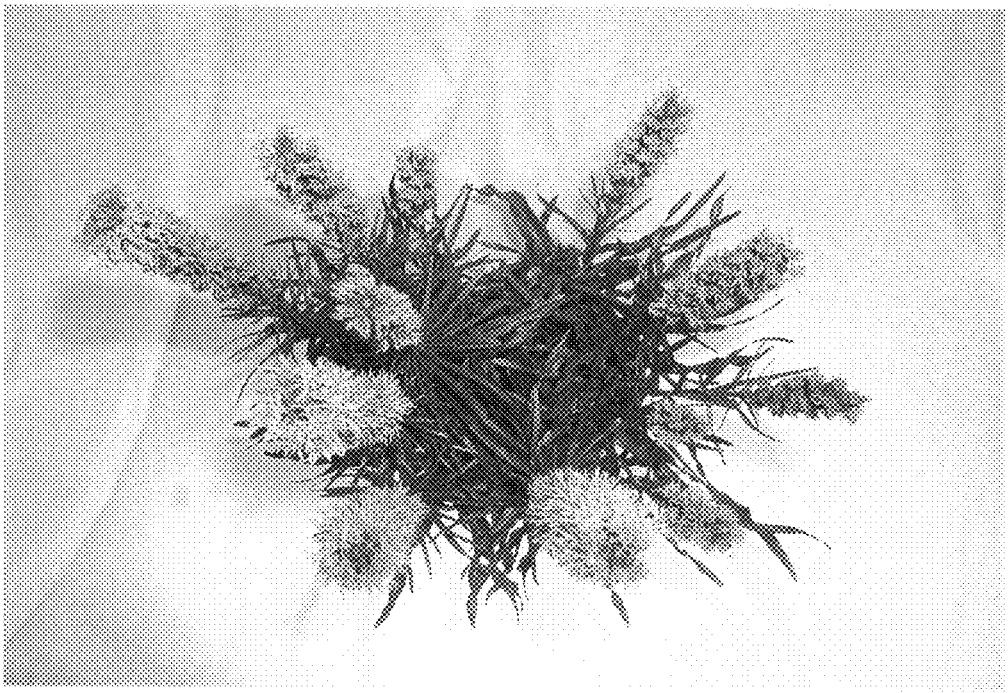
FIG. 2 is a view of the entire plant showing its form, growth habit, foliage, and inflorescence.
Figure 3:
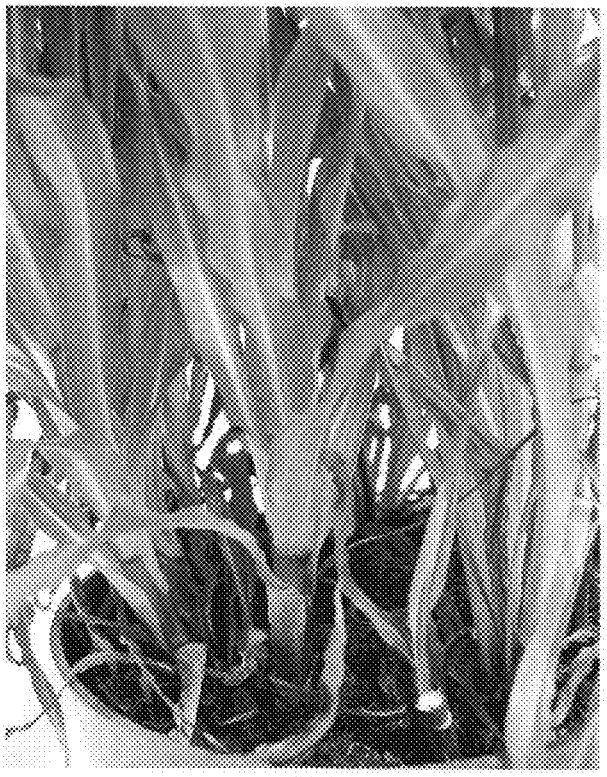
FIG. 3 is a close-up view of the base of the plant.
Figure 4:
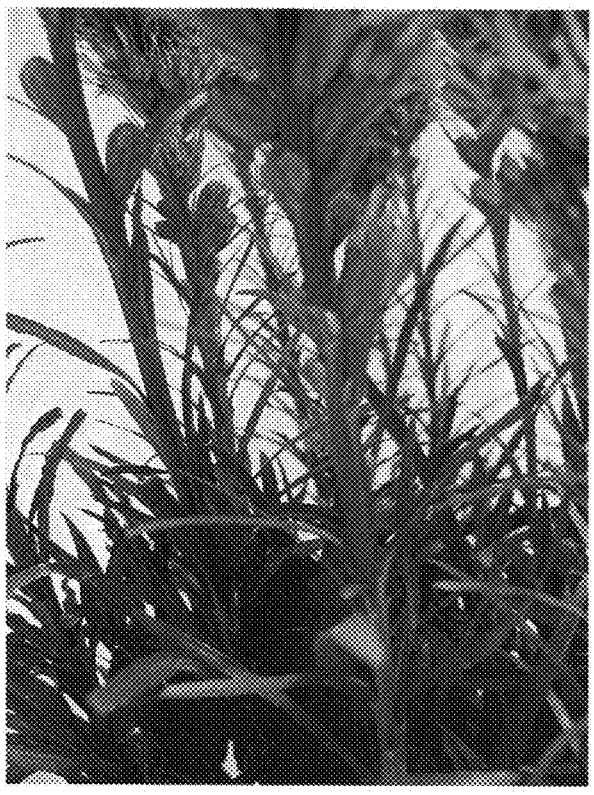
FIG. 4 is a close-up view of inflorescences of the new variety.
Figure 5:
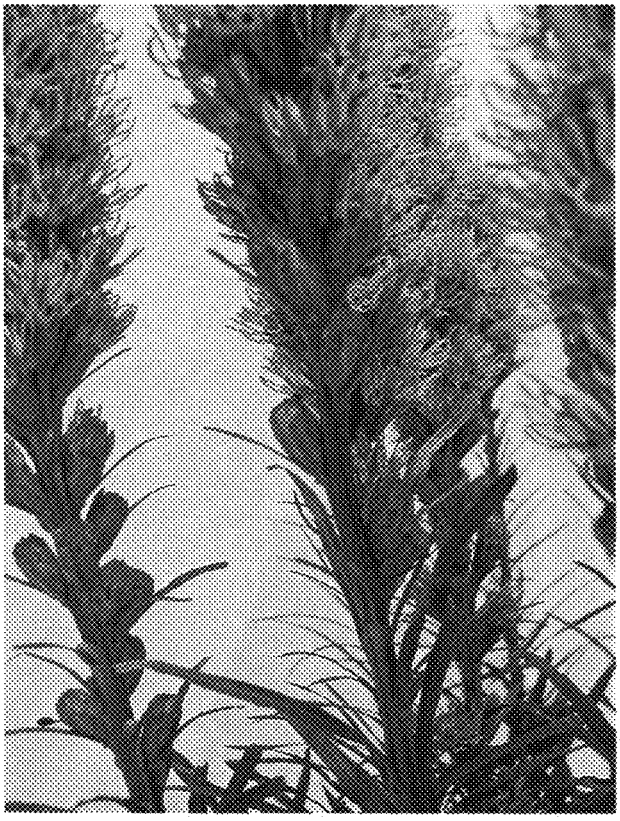
FIG. 5 is a close-up view of inflorescences of the new variety.

The plant shown in the figures is approximately a year old. The plant started out as cuttings, taken from a grown plant.

'BCLT-08.001' has not been observed under all possible environmental conditions. The phenotype may vary significantly with variations in environment such as temperature, light intensity and day length. Color determinations were made with The Royal Horticultural Society (R.H.S.) Colour Chart, in association with the Flower Council of Holland, located in Lieden.

The plant:

*Origin.*—Open controlled cross of *Liatris spicata* var. 'Cobalt'. The plant blooms in the late spring. The plants prefer cool and bright conditions. The blooms typically last 2 to 3 weeks.

*Form.*—Upright, compact perennial. A typical plant with a mature inflorescence that is ready for sale is approximately 20" high and has a diameter of 12" when grown in a 6" pot with appropriate soil amendments.

*Growth.*—Upright, vigorous growth habit. Inflorescence is a raceme and is large. Sap watery. The plant consists of many stems grown from a single root. No lateral branching.

*Stems.*—1 to 5. Stiff/erect. The surface of young stems is glabrous. Stems become woody as they age. The older/lower portions of the stems are R.H.S. 59 C (red-purple group) and 5 mm in diameter. Middle portions of the stems, with no buds or inflorescences, are 5 mm in diameter and R.H.S. 144 B (yellow-green group).

*Foliage.*—Abundant. Leaves alternate on stem. Progressively reduced in size upward. Shape of leaf. — Simple. Linear to lanceolate at end. Margins are entire. Margins are wavy. On some leaves the abaxial and adaxial surfaces reverse. Venation. — Parallel. A central vein dominates on the underside of the leaf. Texture. — Puberulent/slightly hairy; top and bottom surfaces same. Color. — Midvein and majority of leaf surfaces are R.H.S. 145 D (yellow-green group) just above leaf attachment. Developed and fully expanded foliage, both upper and lower surfaces, are 137 A (green group). Leaves are as wide as 12 mm and 18.5 cm long at base of plant. No petioles present.

Buds:

*Form.*—Globose with wavy, imbricate, lanceolate to deltoid, smooth bracts. Buds can be 12 mm long and still unopened. Bracts on mature buds are R.H.S. 139 C (green group) with tips that are R.H.S. 72 B (red-purple group). Aspect. — Smooth. Arrangement. — Sessile.

Inflorescence:

*Form.*—Racemose. Terminal, with younger disk heads developing below. As many as 140 disks per inflorescence. Flowers do not produce a fragrance. The rachis for the raceme is strong and upright. Rachis is R.H.S. 60 B (red-purple group) and 4 mm in diameter. Florets have anthers and style. Racemes are long-lasting, up to three weeks. Shape: Racemose. Size of Inflorescence: Elongated raceme. A typical inflorescence can grow as large as 4 cm. in diameter, and 15 cm high. Appearance: Showy. Sessile flower heads and involucral bracts. Discoid flower head. Flat. 7-13 tube flowers per head. Involucral bracts — imbricate in several rows. Bracts are lanceolate, margins are scarious. No chaff. Bracts are striated, alternately between R.H.S. 145 D (yellow-green group) and R.H.S. 137 A (green group) at base and tips that are R.H.S. 72 B (red-purple group). Receptacle is 2 to 3 mm in diameter. Bracts range in size from 10 mm to 20 mm tall and 10 mm wide.

Florets:

*General.*—Epigynous — growing on top of the ovary. Only tubular flowers. Disk flowers perfect and complete. Corolla: Tubular. 5 — merous. Petals are typically 6 mm long. Tube is 5 mm long. Petal color — base R.H.S. 155 A (white group). Tip R.H.S. 77 B (purple group). Stamens. — 5 stamens. Filament is approximately 5 mm long. Filament is R.H.S. 155 A (white group). Anther is 2 mm long. United by their anthers. Anthers are R.H.S. 79 A (purple group). Stigma. — One style each. Blunt. Style is typically 15 mm long. The 5 mm at the base is R.H.S. 155 A (white group). The upper 10 mm at its tip is and R.H.S. 77 B (purple group). Each style has two stigmas. Ovary. — Ovary is inferior. R.H.S. 145 C (yellow-green group). 5 mm long by 2 mm wide. Calyx/Pappus: General. — Many pilose bristles. Aspect. — smooth and glaucescent. Shape. — linear. Size. — 6 mm long. Color. — R.H.S. 145 D (yellow green group) at base and R.H.S. 72 B (red-purple group) at tips.

*Fruit.*—Not observed.

*Disease resistance.*—Resistant to *Pythium.*

I claim:

1. A new and distinct *Liatris spicata* (L.) Willd. plant named 'BCLT-08.001' substantially as herein shown and described.

* * * * *